United States Patent [19]

Ishibashi et al.

[11] 4,451,567
[45] May 29, 1984

[54] METHOD FOR PRETREATMENT OF CELLULOSIC MATERIALS

[75] Inventors: Tadashi Ishibashi; Masahiko Ishida; Yoji Odawara, all of Hitachi, Japan

[73] Assignee: Hitachi, Ltd., Tokyo, Japan

[21] Appl. No.: 288,467

[22] Filed: Jul. 30, 1981

[30] Foreign Application Priority Data

Jul. 31, 1980 [JP] Japan .................... 55-104285

[51] Int. Cl.³ .......................... C12P 19/14
[52] U.S. Cl. .................. 435/170; 435/171; 435/68; 435/99; 435/105; 435/911; 435/945; 162/65
[58] Field of Search .......... 162/65; 435/99, 68, 435/105, 170, 171, 945, 911

[56] References Cited

U.S. PATENT DOCUMENTS 4,181,796 1/1980 Dietrichs et al. .............. 162/65
4,196,043 4/1980 Singh ........................... 162/65

FOREIGN PATENT DOCUMENTS 56-124394 9/1981 Japan .......................... 435/99

PUBLICATIONS

Tappi, Vol. 54 No. 4, April 1971 pp. 581-584.

Primary Examiner—William F. Smith
Attorney, Agent, or Firm—Antonelli, Terry & Wands

[57] ABSTRACT

The disclosure is concerned with a pretreatment process for removing lignin from lignocellulosic material so as to enhance enzymatic or microbial decomposability of cellulose. The pretreatment process comprises wetting lignocellulosic material with an alkaline aqueous solution in a manner that interstices between the cellulosic material remain, and exposing the wetted cellulosic material to an ozone-containing gas so as to decompose lignin in the lignocellulosic material with a very small energy consumption.

15 Claims, 4 Drawing Figures

METHOD FOR PRETREATMENT OF CELLULOSIC MATERIALS

BACKGROUND OF THE INVENTION

The present invention relates to a method for the pretreatment of cellulosic materials. More particularly, the present invention relates to a method for the pretreatment of lignocellulosic materials for improving a biologically or enzymatically converting lignocellulosic materials.

When microorganism proteins are prepared by reacting a cellulosic material such as rice straw, wheat straw, bagasse, waste paper or wood dust with a cellulose decomposing fungus or bacterium and propagating a cellulase or organic acid secreted by the cellulose decomposing fungus or bacterium, or when an alcohol and an organic acid are prepared by reacting a cellulosic material with a cellulase to convert cellulose to glucose and then reacting the so treated cellulosic material with an enzyme or bacterium, since the cellulosic material has a structure which hardly undergoes the action of a cellulase, it is necessary to adapt a pretreatment for destroying this structure.

Cellulose of a lignocellulosic material is composed of a homopolymer comprising glucose units linearly arranged through $\beta$-1,4 linkages, and cellulose has a crystalline structure in which these linear homopolymers are arranged in parallel to one another and it is covered with hardly decomposable lignin. The cellulase secreted by the cellulose decomposing fungus or bacterium is a composite enzyme comprising $C_1$ enzyme rendering crystalline cellulose amorphous, $C_x$ enzyme decomposing amorphous cellulose into cellobiose and $\beta$-blucosidase decomposing cellobiose to glucose. However, since this composite enzyme has no function of decomposing lignin, the enzyme can hardly react directly with cellulose. Furthermore, cellulases secreted from cellulose decomposing fungi or bacteria isolated up to the present are weak in the activity of rendering crystalline cellulose amorphous, that is, the $C_1$ activity. Accordingly, since cellulose in a cellulosic material is hardly decomposed by presently available cellulases, in order to increase the efficiency of converting the cellulosic material to valuable substances such as glucose and microorganism proteins by the biological decomposition of the cellulosic material, a pretreatment should be carried out for decomposing lignin and for reducing crystallinity of cellulose.

There are three categories of pretreatments known in the art: (See "Physical and Chemical Pretreatments for Enhancing Cellulose Saccharification" by Merril et al, pp 125–153 (1976), and "Production of Microorganic Protein from Residues and Wastes" by T. Ishihara, LUMBER INDUSTRY, vol 34-5 (1979)).

(1) Chemical Pretreatment where various chemical substances are used. Among the chemical substances are exemplified ozone, sodium chloriteacetic acid, boiling caustic soda solution, boiling hydrochloric acid solution, aqueous ammonia solution, aqueous sulfuric acid solution, ethylamine, and phosphoric acid solution.

Ozone and sodium chlorite are used in combination as an oxidizing agent for lignin in lignocellulosic material. Sulfuric acid, hydrochloric acid and phosphoric acid are used to lessen crystallinity of cellulose. These chemical agents do not satisfactorily increase the degree of enzymatic saccharization of cellulose.

(2) Physical Pretreatment including finely grinding with ball-mill, irradiation with $\gamma$-rays and irradiation with ultra-violet rays. These physical pretreatment methods have almost no practical value because they need a large amount of energy.

(3) Microbiological Pretreatment with bacteria for destroying cellulose or hemicellulose or with bacteria for decomposing lignin. These microbiological processes generally require a long period of time because of their slow microbial reaction rate.

After an extensive study of the pretreatments, it has been revealed that chemical pretreatments have advantages over other pretreatments.

In one of the known ozone pretreatments powdered cellulose is dispersed and suspended in water and an ozone-containing gas is supplied into the suspension, whereby ozone reacts with lignin and decomposes it. As the $O_3$-lignin reaction takes place, lignin is decomposed to produce low molecular weight compounds, which react with ozone and consume ozone. Accordingly, the above-mentioned ozone treatment needs a very large amount of ozone.

In the other process of ozone pretreatment, an ozone-containing gas is contacted with powdered dry or wet cellulose to chemically decompose lignin therein. This process needs a large amount of ozone because reactivity between lignin in dry or wet cellulose and ozone is not high.

On the other hand, a known alkaline pretreatment uses an aqueous caustic soda solution in which powdered cellulose is dispersed and suspended in the caustic soda solution and the suspension is heated to extract lignin from the cellulose. In this process, about 200 g of NaOH per 1 kg of rice straw is needed, which is also too much expensive for the commercial use.

When ozone pretreatment is applied to the other chemical pretreatments such as processes using methanol-hydrochloric acid, aqueous ammonia or ethylamine, ozone is consumed in large amounts because $CH_3OH$, $NH_4OH$ and ethylamine react with ozone, rather than with lignin.

Soluble lignin contained in waste water discharged from the step of pulping wood in the paper-making industry is decomposed by ozone (see the research of Takamasa Higuchi, sponsored by the Ministry of Education in 1975 and entitled "Decomposition of Lignin in Waste Water by Treatments with Ozone and Microorganisms; Research Report of Purification of Environment"). Ultraviolet ray decomposition of cellulose is performed at a higher efficiency in an air atmosphere than in a nitrogen atmosphere (see General Organic Chemistry, Natural Polymeric Compounds, Volume I, page 42, published by Asakura Shoten).

In view of the foregoing known facts, we examined applicability of an ozone treatment as the pretreatment of cellulosic materials. At first, as in the treatment of lignin-containing waste water, a cellulosic material was suspended in water and an ozone-containing gas was blown into the suspension to effect an ozone treatment. However, no substantial effect could be obtained. Therefore, we furthered investigations on the ozone treatment, and we found that when a lignocellulosic material, which is impregnated with an alkaline aqueous solution of an alkali metal or alkaline earth metal compound, especially sodium hydroxide, is contacted and reacted with ozone in the state of gas-solid contact, the biological decomposability of the cellulosic material can be remarkably improved.

SUMMARY OF THE INVENTION

It is therefore a primary object of the present invention to provide a method for the pretreatment of lignocellulosic material.

It is another object of the present invention to provide a pretreatment method for effectively removing lignin from lignocellulosic material with a very small energy.

In accordance with the present invention, there is provided a method for the pretreatment of lignocellulosic materials, which comprises wetting a cellulosic material with an alkaline aqueous solution of an alkali metal or alkaline earth metal compound and then contacting the wetted cellulosic material with ozone in the state of gas-solid contact. Interstices of the chopped lignocellulosic material should remain so that ozone can preferentially and easily react with lignin in the cellulosic material.

According to the present invention, the utilizability of a lignocellulosic material by a cellulolytic fungus or bacterium and the enzymatic decomposability of cellulose by the cellulase can be improved the the above-mentioned pretreatment.

As the cellulosic material, there are exemplified rice straw, wheat straw, bagasse, waste paper and wood dust. These cellulosic materials are used after they have been chopped into 0.5 to 10 mm, preferably 5 to 10 mm in length, for example.

Sodium hydroxide is most suitable among the alkali metal or alkaline earth metal compounds. Other compounds are lithium hydroxide, calcium hydroxide, magnesium hydroxide, sodium bicarbonate or in combination thereof.

The cellulosic material is impregnated with such compound in the form of an alkaline aqueous solution.

An alkaline aqueous solution is necessary to loose lignin contained in lignocellulosic material. The final water content of the lignocellulosic material to be treated is preferably controlled to 10 to 80% by weight. When a wet lignocellulosic material is used, the water content thereof is taken into consideration in impregnation. When the water content is lower than 10%, the degree of loosing lignin may be insufficient. When the water content exceeds 80%, a good gas-solid contact between ozone and lignocellulosic material may not be expected. According to the study by the inventors, it has been found that a preferable range of the water content is about 40 to 60% by weight.

The final content of the alkali metal or alkaline earth metal compound in the impregnated lignocellulosic material plays an important role. If the alkali metal or alkaline earth metal compound content is less than 0.001% by weight based on the total weight, the degree of loosing of lignin may be insufficient, which results in the difficulty of decomposition of lignin by ozone treatment. When the content of the compound is larger than 10% by weight, no substantial further improvement is attained.

Preferably, the content of the compound is 0.01 to 1% by weight. If the amount of the compound is based on the dry cellulosic material, a preferable amount is within a range of 0.1 to 10% by weight. When the mixing ratio of the alkaline aqueous solution to the cellulosic material is too large, which results in increase in the amount of water, the chopped cellulosic material adhere to one another and the area of contact with ozone is decreased. Furthermore, soluble lignin dissolved in water preferentially reacts with ozone, which results in consumption of ozone. If the mixing ratio is adjusted within the above-mentioned range of from 0.1 to 10, the cellulosic material is in a gas-solid contact with an ozone-containing gas.

In the present invention, it is preferred that the ozone treatment be carried out at a temperature of 0° to 100° C. and an ozone concentration of about 0.1 to about 20 g/m$^3$.

We examined various conditions for the ozone treatment of cellulosic materials impregnated with an alkaline aqueous solution by using an experimental apparatus described below. The present invention will now be described with reference to the scheme of the apparatus, the operation and the experimental results.

DETAILED DESCRIPTION OF THE PRESENT INVENTION

Figure 1:
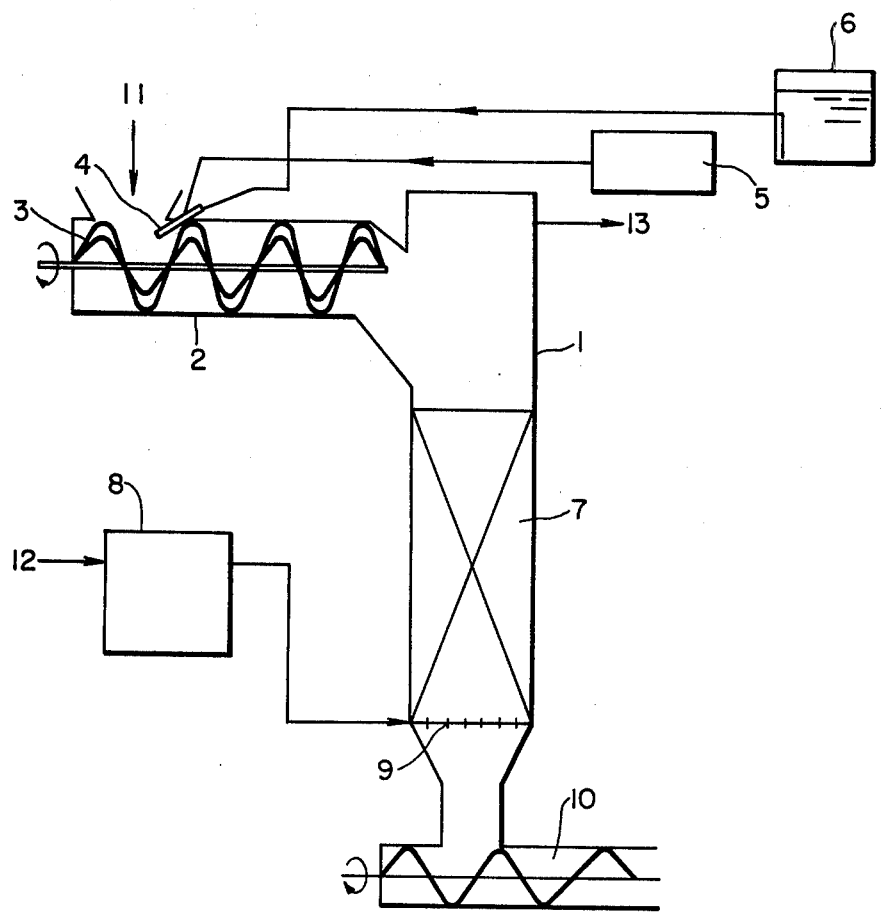
FIG. 1 is a diagram illustrating the section of an apparatus used at experiments according to the present invention.

FIG. 1 is a diagram illustrating the section of the apparatus used at the experiments. The apparatus comprises an ozone treatment tank 1, a mixing tank 2, a stirring vane 3, an atomizer 4, a compressor 5, an alkaline aqueous solution store tank 6, a moving bed 7, an ozone generator 8, an ozone blow opening 9, a discharge feeder 10, a starting material 11, air 12 and an exhaust gas 13.

In the present apparatus, a cellulosic material is impregnated with an alkaline aqueous solution in the mixing tank 2 and is then contacted with ozone in the ozone treatment tank 1.

The alkaline aqueous solution is sprayed on the cellulosic material as the starting material 11 from the atomizer 4 in the vicinity of an inlet of the mixing tank 2. The atomizer 4 sprays the alkaline aqueous solution fed from the alkaline aqueous solution store tank 6 with the aid of compressed air from the compressor 5. The cellulosic material impregnated with the alkaline aqueous solution by spraying is stirred by the stirring vane 3 in the mixing tank 2 and is then fed to the ozone treatment tank 1 and accumulated therein. Then, the cellulosic material is withdrawn from the lower portion of the ozone treatment tank 1 by the discharge feeder 10. During this period, the cellulosic material impregnated with the alkaline aqueous solution is gradually brought down. Ozone-containing air prepared in the ozone generator 8 is blown into the ozone treatment tank 1 from the ozone blow opening 9 located in the lower portion of the ozone treatment tank 1. The cellulosic material impregnated with the alkaline aqueous solution is contacted with the ozone-containing air in a counter-current manner, and the cellulosic material is reacted with ozone and the ozone-containing gas is consumed in the ozone treatment tank 1 and discharged outside the apparatus.

The present invention will now be described in detail with reference to the following Examples that by no means limit the scope of the invention.

EXAMPLE 1

Rice straw cut into a length of 5 to 10 mm was used as the cellulosic material, and it was impregnated with an alkaline aqueous solution and subjected to the ozone treatment. The enzymatic decomposability of rice straw cellulose by a cellulase was then examined.

Sodium hydroxide (hereinafter referred to as "NaOH") was used as the alkaline substance, and various aqueous solutions of NaOH differing in concentration in the range of 0.001 to 20% by weight were prepared. The rice straw was mixed with the aqueous solution of NaOH at a weight ratio of 1/1 to impregnate the rice straw with the aqueous solution of NaOH. The final content of NaOH is 0.1 mg to 2 g per 10 g of dry cellulose and the water is 8 to 10 g per 10 g of dry cellulose. Accordingly, the NaOH content is 0.0005 to 10% by weight based on the total weight of the aqueous solution and cellulosic material. The ozone concentration in ozone-containing air to be blown into the ozone treatment tank 1 was kept at a constant level of 12 g/m$^3$, and the treatment was carried out at room temperature (21±2° C.).

The enzymatic decomposability of each of the so-treated rice straws by a commercially available cellulase (derived from *Trichoderma reesei* and supplied by Amano Seiyaku Kabushiki Kaisha) was measured. The enzymatic decomposability was defined as the amount (mg) of glucose formed for 1 hour by one unit of the enzymatic activity of the cellulase (1 U: the amount of the cellulase forming 1 μ-mole of glucose for 1 minute by 1 ml of the enzyme solution by using carboxymethyl cellulose as the substrate). At the measurement, 100 mg (dry weight) of the treated rice straw was mixed with 2 ml of a 1/20 M citric acid buffer solution (having a pH value of 4.8) and 2 ml of the enzyme solution, and the mixture was shaken at 50° C. for 1 hour. After completion of the reaction, the enzyme was deactivated and the amount of the reducing sugar formed was measured.

For comparison, the measurement was carried out on a sample which had not been subjected to the ozone treatment.

Figure 2:
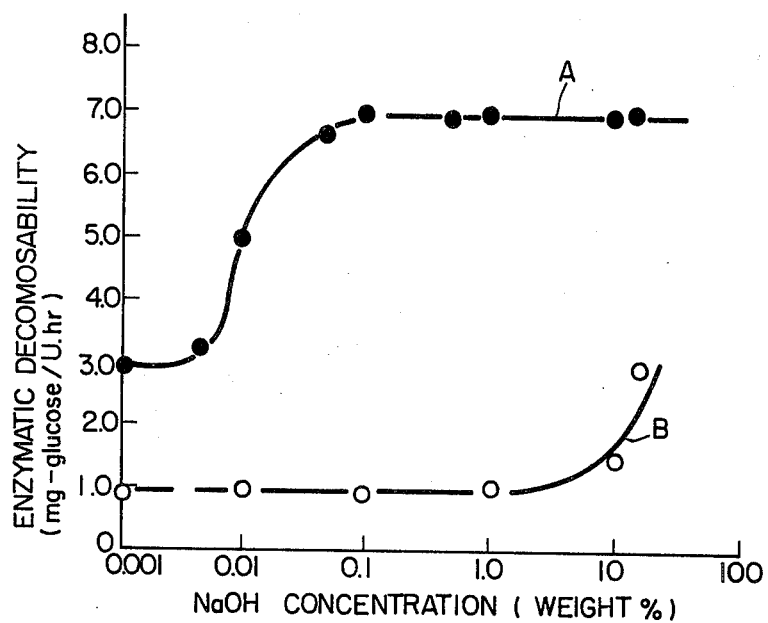
FIG. 2 is a graph illustrating the relation between the concentration of an aqueous solution of NaOH and the enzymatic decomposability.

The obtained results are shown in FIG. 2. Namely, FIG. 2 is a graph illustrating the relation between the concentration of the aqueous solution of NaOH and the enzymatic decomposability. In FIG. 2, curve A shows the results obtained according to the present invention and curve B shows the results obtained when the ozone treatment was not carried out.

As is seen from the graph of FIG. 2, when the concentration of the aqeuous solution of NaOH was 0%, that is, water alone was used, and the impregnated rice straw was subjected to the ozone treatment, the enzymatic decomposability was 3.1 mg-glucose/U·hour at highest, and if the concentration of the aqueous solution of NaOH was 0.005% by weight or higher, the enzymatic decomposability was improved. Furthermore, if the concentration of the aqueous solution of NaOH was higher than 5% by weight, even if the impregnated rice straw was not subjected to the ozone treatment, the enzymatic decomposability was improved, but the degree of improvement was much lower than in case of the impregnated rice straw which had been subjected to the ozone treatment.

EXAMPLE 2

The treatment was carried out in the same manner as described in Example 1, and the amount of ozone reacted per 1 kg (dry weight) of the rice straw was measured.

The amount of reacted ozone was calculated from the difference of the ozone concentration between the inlet and outlet of the ozone treatment tank 1, the feed rate of the ozone-containing air and the contact time.

Figure 3:
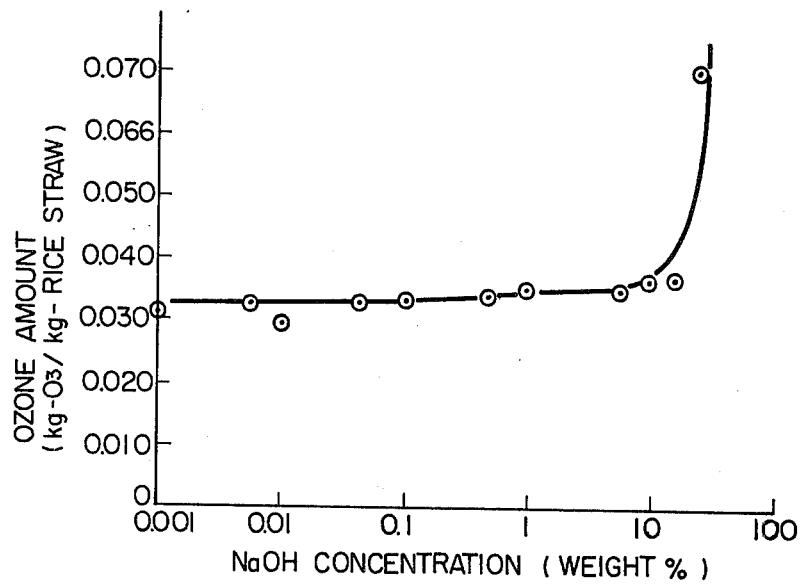
FIG. 3 is a graph illustrating the relation between the concentration of an aqueous solution of NaOH and the amount of ozone reacted.

The obtained results are shown in FIG. 3 which is a graph showing the relation between the concentration of the aqueous solution of NaOH and the amount of reacted ozone. As is seen from FIG. 3, the amount of reacted ozone was abruptly increased when the concentration of the aqueous solution of NaOH exceeded 15% by weight. In the light of the results shown in FIG. 2, it is seen that if the concentration of the aqueous solution of NaOH is higher than 15% by weight or the content of NaOH is larger than about 10% based on the total weight of the aqueous solution and cellulose, the amount of reacted ozone is consumed by the alkaline compound and the enzymatic decomposability is hardly increased. Accordingly, it is considered that this increased amount of reacted ozone is an apparent amount of reacted ozone and the enzymatic decomposability is not substantially improved but ozone is merely decomposed by the alkali.

From the results obtained in Examples 1 and 2, it can be concluded that an effective and economical concentration of the aqueous solution of NaOH is in the range from 0.005 to 15% by weight, especially 0.1 to 1% by weight. This amount corresponds to about 0.001 to 10% of an alkaline substance by weight based on the total weight of the alkaline solution and the cellulosic material. Preferably, the content of alkaline substance should be about 0.01 to 1% by weight.

EXAMPLE 3

The concentration of the aqueous solution of NaOH was adjusted to 0.1, 0.5 or 1% by weight, and the relation between the mixing weight ratio of the rice straw and the aqueous solution of NaOH and the enzymatic decomposability was examined.

With respect to each of the aqueous solutions of NaOH, the mixing weight ratio was adjusted within the range of from 0.1 to 20 and the ozone treatment was carried out under the same conditions as adopted in Example 1.

Figure 4:
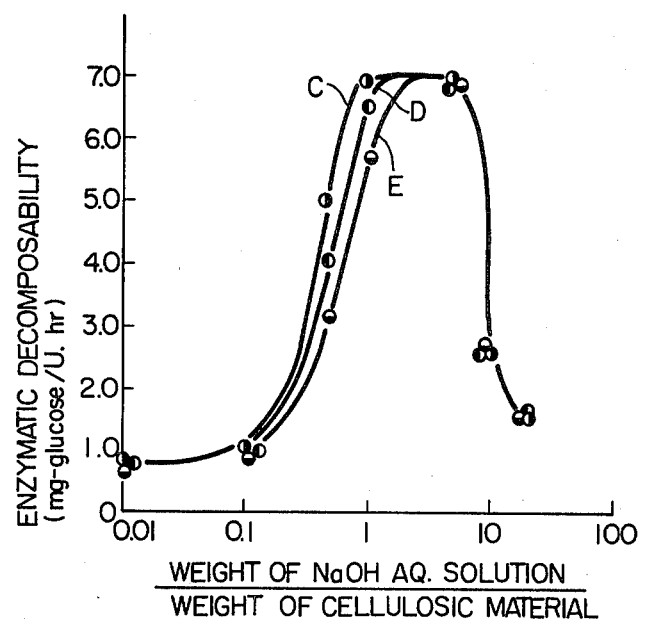
FIG. 4 is a graph illustrating the relation between the mixing ratio of an aqueous solution of NaOH to the enzymatic decomposability.

The obtained results are shown in FIG. 4, which is a graph showing the relation between the mixing weight ratio of the aqueous solution of NaOH and the rice straw and the enzymatic decomposability, and curves C, D and E shows the results obtained when the concentrations of the aqueous solutions of NaOH were 0.1, 0.5 and 1% by weight, respectively.

From FIG. 4, it is seen that in each case, if the mixing weight ratio was at least 0.1, the enzymatic decomposability was improved and especially good results could be obtained when the mixing weight ratio was in the range of from 1 to 7. It also is seen that if the mixing weight ratio exceeded 7, the enzymatic decomposability was reduced and this reduction was extreme if the mixing weight ratio was 20 or higher.

From the foregoing results, it will readily be understood that the mixing weight ratio of the aqueous solution of NaOH to rice straw should be about 0.1 to about 10, preferably 1 to 7. When the content of the aqueous solution is expressed in terms of water content, it should be within a range of about 10 to 80% by weight, preferably about 40 to 60% by weight.

EXAMPLE 4

Bagasse, wood dust, newspaper and corn stover were impregnated separately as the cellulosic material with an aqueous solution of NaOH and was then subjected to the ozone treatment in gas-solid contact, and the enzymatic decomposability was examined. The concentration of the aqueous solution of NaOH was adjusted to 0.1% by weight, and the mixing weight ratio of the aqueous solution of NaOH to the cellulosic material was adjusted to 1. The ozone treatment was carried out under the same conditions as adopted in Example 1. For comparison, the cellulosic material was impregnated with water(water/cellulosic material weight ratio=1/1) and was then subjected to the ozone treatment, and the enzymatic decomposability was examined. Furthermore, the ozone decomposability of the sample which was not subjected to the ozone treatment (untreated sample) was examined.

The obtained results are shown in Table 1.

TABLE 1

| Cellulosic Material | Treatment | Enzymatic Decomposability (mg-glucose/ U · hour) |
|---|---|---|
| bagasse | impregnation with NaOH aqueous solution and ozone treatment in gas-solid contact | 6.8 |
| " | impregnation with water and ozone treatment in gas-solid contact | 3.3 |
| " | untreated | 1.2 |
| wood dust | impregnation with NaOH aqueous solution and ozone treatment in gas-solid contact | 5.2 |
| " | impregnation with water and ozone treatment in gas-solid contact | 2.5 |
| " | untreated | 0.5 |
| newspaper | impregnation with NaOH aqueous solution and ozone treatment in gas-solid contact | 4.2 |
| " | impregnation with water and ozone treatment in gas-solid contact | 2.8 |
| " | untreated | 1.6 |
| corn stover | impregnation with NaOH aqueous solution and ozone treatment in gas-solid contact | 5.8 |
| " | impregnation with water and ozone treatment in gas-solid contact | 3.0 |
| " | untreated | 1.0 |

From the results shown in Table 1, it will readily be understood that excellent effects can be obtained according to the method of the present invention.

EXAMPLE 5

Sodium hydroxide, potassium hydroxide, lithium hydroxide, sodium bicarbonate, calcium hydroxide and magnesium hydroxide were used as the alkali metal or alkaline earth metal compound, and the effects were examined.

Rice straw was used as the cellulosic material. The concentration of each alkaline aqueous solution was adjusted to 1.0% by weight, and the mixing weight ratio of the alkaline aqueous solution to rice straw was adjusted to 1. The ozone treatment was carried out under the same conditions as adopted in Example 1. The enzymatic decomposability of each treated rice straw was examined in the same manner as described in Example 1. The obtained results are shown in Table 2.

TABLE 2

| Alkali Metal or Alkaline Earth Metal Compound | Enzymatic Decomposability (mg-glucose/U · hour) |
|---|---|
| sodium hydroxide | 7.0 |
| potassium hydroxide | 6.8 |
| lithium hydroxide | 6.0 |
| sodium bicarbonate | 4.2 |
| calcium hydroxide | 5.5 |
| magnesium hydroxide | 3.8 |

From the results shown in Table 2, it will readily be understood that even when alkali metal or alkaline earth metal compounds in place of sodium hydroxide are used, the enzymatic decomposability can be improved since the enzymatic decomposabilities of water-impregnated ozone-treated and untreated rice straw are about 3.0 mg-glucose/U·hour and about 0.9 mg-glucose/U·hour, respectively.

EXAMPLE 6

The utilizability of rice straw impregnated with an aqueous solution of NaOH and treated with ozone, by a cellulose decomposing fungus was examined to find whether or not cellulose of such rice straw could be utilized as a nutritive source.

The concentration of the aqueous solution of NaOH was adjusted to 0.1% by weight, and the mixing weight ratio of the aqueous solution of NaOH to rice straw was adjusted to 1. As the cellulose decomposing fungus, there were used *Trichoderma reesei* American Type Culture Collection (ATCC) no. 13631 and *Cellulomonas flavigena* (ATCC No. 484).

A culture medium used for culturing comprised 6.0 g/l of sodium chloride, 1.0 g/l of ammonium sulfate, 0.5 g/l of monopotassium phosphate, 0.5 g/l of dipotassium phosphate, 0.2 g/l of magnesium sulfate, 0.3 g/l of calcium chloride and 1.0 g/l of yeast extract. The concentration of rice straw was adjusted to 10 g/l. Culturing was conducted at 30° C. for 10 days.

As the index of the utilizability by the cellulose decomposing fungus, the amount of proteins formed by the cellulose decomposing fungus was determined by subtracting the amount of protein contained in the rice straw from the protein contained in the culture medium. The obtained results are shown in Table 3. For comparison, the experiment was carried out without performing the ozone treatment (untreated). The obtained results are also shown in Table 3.

TABLE 3

| Cellulose Decomposing Fungus | Treatment | Amount of Formed Protein (g-protein per g-dry rice straw) |
|---|---|---|
| *Trichoderma reesei* | impregnation with NaOH aqueous solution and ozone treatment in gas-solid contact | 0.075 |
| " | untreated | 0.001 |
| *Cellulomonas flavigena* | impregnation with NaOH aqueous solution and ozone treatment in gas-solid contact | 0.097 |
| " | untreated | 0.015 |

From the results shown in Table 3, it will readily be understood that when impregnation with an aqueous solution of NaOH and ozone treatment are carried out according to the present invention, the amount of propagation of a cellulose decomposing fungus is increased and utilizability of rice straw by the cellulose decomposing fungus can be increased.

As will be apparent from the foregoing description, if a cellulosic material is impregnated with an alkaline aqueous solution of an alkali metal or alkaline earth metal compound and is then contacted with ozone according to the present invention, the biological decomposability characteristics of the cellulosic material, that is, the enzymatic decomposability by a cellulase and the utilizability by a cellulose decomposing fungus, can be improved. Especially good results can be obtained when a cellulosic material is impregnated with sodium hydroxide at a concentration of 0.001 to 10% by weight and at the water content in the cellulosic material of 10 to 80% and the cellulosic material is then subjected to the ozone treatment, keeping gas-solid contact between the cellulosic material and ozone. The method of the present invention is very simple. And, since the amount used of water is small, a problem of the waste water treatment does not occur. Furthermore, the pretreatment method of the present invention can effectively be applied to not only manufacture of glucose and microorganism protein from cellulosic materials but also conversion of cellulosic materials to valuable substances by using microorganisms capable of methane fermentation or organic acid fermentation.

The present invention consumes only a very small amount of energy, because the process uses a small amount of water which dissolves low molecular weight compounds that decompose ozone. Accordingly, required energy for generating ozone is smaller than the process in which cellulosic material is suspended in water. Further, in the process of the present invention the lignin, which is loosed by the impregnated alkaline solution, is effectively decomposed, because ozone can attack the lignin in gas-solid contact.

What is claimed is:

1. A method for biologically or enzymatically converting lignocellulosic materials, which comprises wetting a lignocellulosic material with an alkaline aqueous solution of an alkali metal or alkaline earth metal compound and then contacting the wetted lignocellulosic material with ozone in the state of gas-solid contact, wherein the water content of said wetted lignocellulosic material is 10 to 80% by weight and the content of alkali metal or alkaline earth metal compound is 0.001 to 10% by weight based on the total weight of the alkaline aqueous solution and the cellulosic material, to make loose the lignin from the lignocellulosic material without the lignin going into solution, and wherein the wetted lignocellulosic material is contacted with ozone without the lignin, loosened by the treatment with the aqueous liquid of alkali metal or alkaline earth metal compound, having previously gone into solution, to decompose the loose lignin, and subjecting the treated lignocellulosic material to biological or enzymatic decomposition treatment.

2. A method for biologically or enzymatically converting lignocellulosic material according to claim 1, wherein the water content of the lignocellulosic material is about 40 to 60% by weight.

3. A method for biologically or enzymatically converting lignocellulosic material according to claim 1, wherein the content of alkaline is 0.01 to 1% by weight based on the total weight of the alkaline solution and the lignocellulosic material.

4. A method for biologically or enzymatically converting lignocellulosic material according to claim 1, wherein the cellulosic material is contacted with ozone at a temperature of 0°–100° C. and at an ozone concentration of about 0.1 to about 20 $g/m^3$.

5. A method for biologically or enzymatically converting lignocellulosic material according to claim 1, consisting essentially of the steps of wetting the lignocellulosic material, and then contacting the wetted lignocellulosic material with ozone, and then subjecting the treated lignocellulosic material to biological or enzymatic decomposition treatment.

6. A method for biologically or enzymatically converting lignocellulosic materials according to claim 1, wherein said subjecting comprises exposing the treated lignocellulosic material to cellulolytic fungus or bacterium.

7. A method for biologically or enzymatically converting lignocellulosic material, which comprises impregnating a chopped lignocellulosic material with an aqueous liquid of alkali metal or alkaline earth metal compound in such a manner that interstices of the chopped lignocellulosic material remain, wherein the water content of the impregnated lignocellulosic material is 10 to 80% by weight and wherein the content of alkali metal or alkaline earth metal compound is 0.001 to 10% by weight based on the total weight of the alkali metal or alkaline earth metal compound, water and lignocellulosic material, to make loose the lignin of the lignocellulosic material without the lignin going into solution; contacting the impregnated lignocellulosic material with an ozone-containing gas without the lignin, loosened by said impregnating, having previously gone into solution, keeping gas-solid contact between the ozone-containing gas and the impregnated lignocellulosic material, whereby the lignin is preferentially decomposed by the ozone-containing gas; and subjecting the treated cellulosic material to biological or enzymatic decomposition treatment.

8. A method for biologically or enzymatically converting lignocellulosic material according to claim 7, wherein alkali metal compound is sodium hydroxide.

9. A method for biologically or enzymatically converting lignocellulosic material according to claim 7, wherein the amount of alkali metal or alkaline earth metal compound is 0.1 to 10% by weight based on the dry lignocellulosic material.

10. A method for biologically or enzymatically converting lignocellulosic material according to claim 7, wherein said ozone-containing gas has an ozone concentration of about 0.1 to about 20 $g/m^3$, and the impregnated lignocellulosic material contacts said ozone-containing gas at a temperature of 0°–100° C.

11. A method for biologically or enzymatically converting lignocellulosic material according to claim 7, wherein the chopped lignocellulosic material is 0.5 to 10 mm in length.

12. A method for biologically or enzymatically converting lignocellulosic material according to claim 7, consisting essentially of the steps of impregnating a chopped lignocellulosic material, and contacting the impregnated lignocellulosic material with an ozone-containing gas, and then subjecting the treated cellulosic material to biological or enzymatic decomposition treatment.

13. A method for biologically or enzymatically converting lignocellulosic material according to claim 7, wherein said subjecting comprises exposing the treated lignocellulosic material to cellulolytic fungus or bacterium.

14. A method for biologically or enzymatically converting lignocellulosic material according to claim 1 or 7, wherein the alkali or alkaline earth metal compound is selected from the group consisting of sodium hydroxide, lithium hydroxide, calcium hydroxide, magnesium hydroxide, sodium bicarbonate and mixtures thereof.

15. A method for biologically or enzymatically converting lignocellulosic material according to claim 1 or 7, wherein the lignocellulosic material is selected from the group consisting of rice straw, wheat straw, bagasse, waste paper and wood dust.

* * * * *